United States Patent
Skolnick et al.

(10) Patent No.: US 8,354,377 B2
(45) Date of Patent: Jan. 15, 2013

(54) USE OF FACTOR VIIA OR FACTOR VIIA EQUIVALENTS FOR PREVENTING OR ATTENUATING HAEMORRHAGE GROWTH, AND/OR OEDEMA GENERATION FOLLOWING INTRACEREBRAL HAEMORRHAGE (ICH) IN A SELECTED SUBPOPULATION OF ICH PATIENTS

(75) Inventors: Brett Skolnick, Philadelphia, PA (US); Nikolai Constantin Brun, Copenhagen N (DK); Kamilla Begtrup, Allerød (DK)

(73) Assignee: Novo Nordisk Health Care AG, Zurich (CH)

( * ) Notice: Subject to any disclaimer, the term of this patent is extended or adjusted under 35 U.S.C. 154(b) by 175 days.

(21) Appl. No.: 12/812,684

(22) PCT Filed: Jan. 16, 2009

(86) PCT No.: PCT/EP2009/050488
§ 371 (c)(1),
(2), (4) Date: Sep. 9, 2010

(87) PCT Pub. No.: WO2009/090240
PCT Pub. Date: Jul. 23, 2009

(65) Prior Publication Data
US 2011/0014179 A1    Jan. 20, 2011

Related U.S. Application Data

(60) Provisional application No. 61/025,387, filed on Feb. 1, 2008.

(30) Foreign Application Priority Data

Jan. 18, 2008  (EP) .................................. 08100633
Jan. 25, 2008  (EP) .................................. 08100916

(51) Int. Cl.
*A61K 38/00* (2006.01)
(52) U.S. Cl. ....................... 514/14.3; 530/383
(58) Field of Classification Search ................. 514/14.3; 530/383
See application file for complete search history.

(56) References Cited

U.S. PATENT DOCUMENTS

| | | | |
|---|---|---|---|
| 2003/0073638 A1 | 4/2003 | Kjalke | |
| 2007/0243183 A1* | 10/2007 | Brun et al. | 424/94.64 |
| 2009/0156481 A1* | 6/2009 | Brun et al. | 514/12 |

FOREIGN PATENT DOCUMENTS

| | | | |
|---|---|---|---|
| EP | 1216709 | | 6/2002 |
| WO | WO98/58661 | | 12/1998 |
| WO | WO02/062376 | | 8/2002 |
| WO | WO03/093465 | | 11/2003 |
| WO | WO2005/123118 | | 12/2005 |
| WO | WO 2007/009895 | * | 1/2007 |
| WO | WO2007/009895 | | 1/2007 |

OTHER PUBLICATIONS

Mayer S. et al. Recombinant Activated Factor VII for Acute Intracerebral Hemorrhage. NEJM Feb. 24, 2005:352(8)777-85.*
John David Morenski et al. Neurosurgery Recombinant Activated Factor VII for Cerebral Injury-Induced Coagulopathy in Pediatric Patients 2003 98 3 611-616.
Park, P. et al. Neurosurgery Recombinant Activated Factor VII for the Rapid Correction of Coagulopathy in Nonhemophilic Neurosurgical Patients 2003 53 1 34-39.
Pier Mannuccio Mannucci. M.D. The New England Journal of Medicine Hemostatic Drugs 1998 339 4 245-253.
Shounika Rinshou Clinical Pediatrics Clinical Pediatrics 2004 57 2 179-187.
Arkin, S, Haemostasis, Activated Recombinant Human Coagulation Factor VII Therapy for Intracranial Hemorrhage in Patients With Hemophilia A or B With Inhibitors, 1998, vol. 28, pp. 93-98.
Berwaerts, J et al, Stroke, Prediction of Functional Outcome and In-Hospital Mortality After Admission With Oral Anticoagulant-Related Intracerebral Hemorrhage, 2000, vol. 31, pp. 2558-2562.
Broderick, J P et al, Stroke, Volume of Intracerebral Hemorrhage 1993, vol. 24 (7), pp. 987-993.
Broderick, J. et al, Stroke, Determinants of Intracerebral Hemorrhage Growth an Exploratoru Analysis, 2007, vol. 38, pp. 1072-1075.
Brott, T et al, Stroke, Early Hemorrhage Growth in Patients With Intracerebral Hemorrhage, 1997, vol. 28, pp. 1-5.
Butcher, K et al, Journal of Clinical Neuroscience, Current Intracerebral Haemorrhage Management, 2003, vol. 10(2), pp. 158-167.
Chuansumrit, A MD et al., Journal of the Medical Association of Thailand=Chotmaihet Thang, Outcome of Intracranial Hemorrhage in . . . , 2002, vol. 85, pp. S1059-S1064.
Davis et al., Neurology, Hematoma Growth is a Determinant of Mortality and Poor Outcome After Intercerebral Hemorrhage, 2006, vol. 66, pp. 1175-1181.
Diringer, M.N et al., Blood, use of Recombinant Factor VIIA in Patients With . . . , 2003, vol. 102(11), p. #4144.
Diringer, Michael N. et al., Cerebrovascular Diseases, Impact of Recombinant Activated Factor VII on Health-Related Quality of Life After Intracerebral Hemorrhage, 2007, vol. 24(2-3), pp. 219-225.
Diringer, Michael N. et al., Stroke, Risk of Thromboembolic Events in Controlled Trials of RFVIIA in Spontaneous Intracerebral Hemorrhage, 2008, vol. 39(3), pp. 850-856.
Franke, C L et al, Journal of Neurology Neurosurgery and Psychiatry, Prognostic Factors in Patients With Intracerebral Haematoma, 1992, vol. 55, pp. 653-657.
Fujii, Y et al, Journal of Neurosurgery, Hematoma Enlargement in Spontaneous Intracerebral Hemorrhage, 1994, vol. 80, pp. 51-57.
Hemphill III, J C et al, Stroke, The ICH Score a Simple Reliable Grading Scale for Intracerebral Hemorrhage, 2001, vol. 32, pp. 891-897.

(Continued)

Primary Examiner — Ralph Gitomer
(74) Attorney, Agent, or Firm — Michael J. Brignati

(57) ABSTRACT

The invention relates to a method for preventing or attenuating one or more complications of intracerebral haemorrhage (ICH), the method comprising: (i) selecting an ICH patient who exhibits one or more of the following characteristics: age≦70, baseline ICH volume≦60 mL, baseline IVH volume≦5 mL, and elapsed time since onset of symptoms of less than about 2.5 hours; and (ii) administering to said patient in need thereof an effective amount of a first coagulation agent comprising Factor VIIa or a Factor VIIa equivalent.

8 Claims, No Drawings

OTHER PUBLICATIONS

Kazui, S et al, Stroke, Enlargement of Spontaneus Intracerebral Hemorrhage, 1996, vol. 27, pp. 1783-1787.

Majumdar, G et al., Blood Coagulation and Fibrinolysis, Recombinant Factor VIIA for Intracranial . . . , 1993, vol. 4(6), pp. 1031-1033.

Matsuoka, H et al, CNS Drugs, Role of Thrombin in CNS Damage Associated With Intracerebral Haemorrhage, 2002, vol. 16(8), pp. 509-516.

Mayer, S A., Stroke, Ultra-Early Hemostatic Theraphy for Intracerebral Hemorrhage, 2003, vol. 34, pp. 224-229.

Mayer, S. A et al., Neurocritical Care, Recombinant Activated Factor VII for Acute Intracerebral Hemorrhage, 2006, vol. 4(3), pp. 206-214.

Mayer, S. A et al., The New England Journal of Medicine, Recombinant Activated Factor VII for Acute Intracerebral Hemorrhage, 2005, vol. 352, pp. 777-785.

Mayer, S. A. et al., Seminars in Hematology, Ultra-Early Hemostatic Therapy for Acute Intracerebral Hemorrhage, 2006, vol. 43(1), pp. 70-76.

Mayer, Stephan A. et al., New England Journal of Medicine, Efficacy and Safety of Recombinant Activated Factor VII for Acute Intracerebral Hemorrhage, 2008, vol. 358(20), pp. 2127-2137.

Mayer, Stephan A. et al., Stroke, Can a Subset of Intracerebral Hemorrhage Patients Benefit From Hemostatic Therapy With Recombinant Activated Factor VII?, 2009, vol. 40(3), pp. 833-840.

Portenoy, R K et al., Journal of Neurology Neurosurgery and Psychiatry Intracerebral Haemorrhage: A Model for the Prediction of Outcome, 1987, vol. 50, pp. 976-979.

Rådberg, J A et al., Stroke, Prognostic Parameters in Spontaneous Intracerebral Hematomas Witih Special Reference to Anticoagulant Treatment, 1991, vol. 22, pp. 571-576.

Sacco, S et al., Journal of the Neurologiical Sciences, Medical Treatment of Intracerebral Hemorrhage, 2004, vol. 24, pp. S6-S9.

Skolnick, B et al., Blood, Safety and Laboratory Reaults for Recombinant Activated Coagulation Factor VII in Patients With Acute Intrcerebral Hemorrhage, 2003, vol. 102(11).

Tuhrim, S et al., Annals of Neurology, Prediction of Intracerebral Hemorrhage Survival, 1988, vol. 24(2), pp. 258-263.

Weiskopf, R. B., Vox Sanguinis. Recombinant-Activated Coagulation Factor VIIA (Novoseven): Current Development, 2007, vol. 92(4), pp. 281-288.

Wong, W.Y et al., Haemophilia, Clinical Efficacy and Recovery Levels of Recombinant FVIIA . . . , 2000, vol. 6(1), pp. 50-54.

Mayer, S.A., "Ultra-Early Hemostatic Therapy for Intracerebral Hemorrhage", Stroke, 2002, vol. 34, pp. 224-229.

* cited by examiner

USE OF FACTOR VIIA OR FACTOR VIIA EQUIVALENTS FOR PREVENTING OR ATTENUATING HAEMORRHAGE GROWTH, AND/OR OEDEMA GENERATION FOLLOWING INTRACEREBRAL HAEMORRHAGE (ICH) IN A SELECTED SUBPOPULATION OF ICH PATIENTS

CROSS-REFERENCE TO RELATED APPLICATIONS

This application is a 35 U.S.C. §371 national stage application of International Patent Application PCT/EP2009/050488 (published as WO 2009/090240), filed Jan. 16, 2009, which claimed priority of European Patent Application 08100633.0, filed Jan. 18, 2008 and European Patent Application 08100916.9, filed Jan. 25, 2008; this application further claims priority under 35 U.S.C. §119 of U.S. Provisional Application 61/025,387, filed Feb. 1, 2008.

FIELD OF THE INVENTION

The invention relates to the prevention of, or minimizing severity of complications in selected ICH patients, who exhibit one or more of the following characteristics: age$\leq$70, baseline ICH volume$\leq$60 mL, baseline IVH volume$\leq$5 mL, and elapsed time since onset of symptoms of less than about 2.5 hours. The invention furthermore relates to a method for assessing the suitability of an ICH patient for treatment with Factor VIIa or a Factor VIIa equivalent.

BACKGROUND OF THE INVENTION

Haemostasis is a complex physiological process which ultimately results in the arrest of bleeding. This is dependent on the proper function of three main components: blood vessels (especially the endothelial lining), coagulation factors, and platelets. Once a haemostatic plug is formed, the timely activation of the fibrinolytic system is equally important to prevent further unnecessary haemostatic activation. Any malfunction of this system (due to a reduced number, or molecular dysfunction, of the haemostatic components or increased activation of the fibrinolytic components) may lead to clinical bleeding such as, e.g., haemorrhagic diathesis of varying severity.

In most physiological situations, haemostasis is triggered by the interaction of circulating activated coagulation factor VII (FVIIa) with tissue factor (TF) subsequent to exposure of TF at the site of an injury. Endogenous FVIIa becomes proteolytically active only after forming a complex with TF. Normally, TF is expressed in the deep layers of the vessel wall and is exposed following injury. This ensures a highly localized activation of coagulation and prevents disseminated coagulation. TF also seems to exist in a non-active form, so-called encrypted TF. The regulation of encrypted versus active TF is still unknown.

Intracerebral haemorrhage (ICH) is a neurological condition that occurs spontaneous and results in blood collecting in the intraparenchymal brain tissue. Blood may further collect in the brain ventricles (intraventricular haemorrhage (IVH)). The results of an ICH have been demonstrated to result in significant morbidity and mortality. In recent years ICH has been shown to increase in volume in the hours following the initial insult. This occurs in from approximately 38% (Brott et al., 1997) to 73% (Davis, et al. 2006) of patients suffering from ICH. The reason for the increase is unclear, but it is thought to be either through a continuous oozing of the original haematoma or through a complex process of rebleeds.

Days after the initial insult a zone of oedema can be identified on CT scans—surrounding the blood in the haematoma. The mechanism for oedema generation is also poorly understood but may be due to a combination of an inflammatory reaction in the tissue surrounding the clot as well as a direct mass effect of the clot exerting pressure on surrounding brain tissue. The impact of the isolated oedema can be significant; the effects of oedema on the volume of compromised brain tissue following ICH has been estimated to be up to 3 times the actual volume of the haematoma. The importance of overall effected tissue volume would appear to be one of the strongest predictors of outcome after ICH. Thus there is clinical interest in reducing any haemorrhage expansion and in reducing and/or minimizing the total lesion volume (blood and resulting oedema).

International Publications WO 2005/123118 and WO 2007/009895 relate to the use of Factor VIIa or Factor VIIa equivalents for preventing or attenuating haemorrhage growth, and/or oedema generation following intracerebral haemorrhage (ICH) in patients, including patients having received anticoagulant treatment.

Further trials and analysis have now revealed that a specifically defined subpopulation of patents may benefit in particular from treatment with Factor VIIa or a Factor VIIa equivalent. Thus, there is a further need in the art for improved methods and compositions for acute treatment of ICH, as well as for prevention and attenuation of later complications that result from ICH and from conventional modalities that are used to treat a herein defined subpopulation of patients with ICH.

SUMMARY OF THE INVENTION

The invention provides the use of Factor VIIa or a Factor VIIa equivalent for the manufacture of a medicament for preventing or attenuating one or more complications of ICH in selected ICH patients exhibiting one or more of the following characteristics: Age$\leq$70, baseline ICH volume$\leq$60 mL, baseline IVH volume$\leq$5 mL, and elapsed time since onset of symptoms of less than about 2.5 hours.

The term "selected ICH subpopulation patient" may in the present context be used interchangeably with the term "selected ICH patients exhibiting one or more of the following characteristics: Age$\leq$70, baseline ICH volume$\leq$60 mL, baseline IVH volume$\leq$5 mL, and elapsed time since onset of symptoms of less than about 2.5 hours".

The invention further provides the use of Factor VIIa or a Factor VIIa equivalent for the manufacture of a medicament for preventing or attenuating haemorrhage growth, and/or oedema generation following ICH in selected ICH patients exhibiting one or more of the following characteristics: Age$\leq$70, baseline ICH volume$\leq$60 mL, baseline IVH volume$\leq$5 mL, and elapsed time since onset of symptoms of less than about 2.5 hours.

Typical patients for whom the medicament is used are those suffering from coagulopathic bleedings, including, without limitation, patients who have experienced spontaneous or traumatic ICH.

The invention also provides the use of Factor VIIa or a Factor VIIa equivalent for the manufacture of a medicament for increasing overall survival of a selected ICH subpopulation patient at day 15, such as day 30, day 60, or preferably day 90 following the start of treatment. In another aspect, the invention provides the use of Factor VIIa or a Factor VIIa equivalent for the manufacture of a medicament for reducing the number of days of hospitalization of a selected ICH subpopulation patient, including days in the Intensive Care Unit (ICU), bed confinement, and/or Quality of Life as measured by the European Quality of Life Scale (EuroQOL), or similar instruments, in the period from start of treatment (SOT) to day 15, such as day 30, day 60, or preferably day 90 following the start of treatment or for reducing the risk of death in a selected ICH subpopulation patient. In one embodiment, (i) an amount of 20 or 80 μg/kg of Factor VIIa or Factor VIIa equivalent is administered to the patient at the start of treatment as a slow single bolus but in the setting of additional risk factors (e.g. anti-coagulant or anti-platelet treated patients may result in further dosing).

The invention also provides methods for preventing or attenuating one or more complications of ICH in a selected ICH subpopulation patient, which are carried out by administering to the patient an effective amount of Factor VIIa or a Factor VIIa equivalent. Typical patients have experienced spontaneous or traumatic ICH.

In one aspect of the invention, the initial administering step is carried out within 2.5 hours of the occurrence of the ICH. In some embodiments, the method further comprises administering to the patient a second coagulation agent in an amount that augments the said Factor VIIa or Factor VIIa equivalent effect. Preferably, the second coagulation agent is a coagulation factor (including, without limitation, Factor VIII, Factor IX, Factor V, Factor XI, Factor XIII, and any combination thereof) or an antifibrinolytic agent (including, without limitation, PAI-1, aprotinin, ε-aminocaproic acid, tranexamic acid, or any combination thereof).

The invention also provides methods for reducing the number of days a selected ICH subpopulation patient is hospitalized following ICH, which methods are carried out by administering to the patient an amount effective of Factor VIIa or a Factor VIIa equivalent to achieve the prevention or attenuation of haemorrhage growth, and/or oedema generation following ICH.

The invention also provides methods for reducing the risk of death in a selected ICH subpopulation patient, which are carried out by administering an amount of Factor VIIa or a Factor VIIa equivalent to the patient for preventing or attenuating oedema generation following ICH.

The invention also provides methods for preventing or attenuating one or more complications of ICH in a majority of selected ICH subpopulation patients, which are carried out by: (i) administering to said group of selected ICH subpopulation patients an amount effective for achieving the prevention or attenuation of Factor VIIa or a Factor VIIa equivalent; and (ii) observing a reduction in the frequency of occurrence of one or more complications of ICH among the group of patients who received Factor VIIa or a Factor VIIa equivalent relative to the frequency of occurrence of said complications that would have been expected in the same group of patients who had not received said Factor VIIa or Factor VIIa equivalent.

DETAILED DESCRIPTION OF THE INVENTION

The present invention provides methods and compositions that can be used advantageously to prevent or attenuate haemorrhage growth, and/or oedema generation following ICH, which patients may experience subsequent to their initial injury and/or as a result of medical interventions that may be used to treat their injuries. The methods are carried out by administering to a selected ICH subpopulation patient, Factor VIIa or a Factor VIIa equivalent, in a manner that is effective for preventing or attenuating haemorrhage growth, oedema formation as well as one or more complications related to ICH. A manner effective for preventing or attenuating haemorrhage growth, oedema formation and the subsequent complications may comprise administering a predetermined amount of Factor VIIa or a Factor VIIa equivalent, and/or utilizing a particular dosage regimen, formulation, mode of administration, combination with other treatments, and the like. The efficacy of the methods of the invention in reducing haemorrhage growth, oedema formation or in preventing complications of ICH may be assessed using one or more conventional imaging methods (e.g., CT, MRI scanning) or by use of parameters that evaluate complications (see below). Complications that may be prevented by the methods of the invention, or whose severity may be attenuated, include, without limitation, haemorrhage growth, oedema generation, and decreased quality of life including death caused by one or more of these syndromes.

Patient Selection:

The present inventors have now identified a subpopulation of patients experiencing ICH that may particularly benefit from treatment with Factor VIIa or a Factor VIIa equivalent. The selection criteria for the identified subpopulation comprises one or more of the following characteristics: age≦70 years, baseline ICH volume≦60 mL, baseline IVH volume≦5 mL, and elapsed time since onset of symptoms of less than about 2.5 hours. "Baseline" volume means volume measured at time of diagnosis (for example, by use of imaging by CT or MR scans, e.g. as described below). "Baseline ICH volume" and baseline IVH volume" thus, respectively, means volume of intracerebral haemorrhage (blood collecting in the intraparenchymal brain tissue) measured at time of diagnosis and volume of intraventricular haemorrhage (blood collecting in the brain ventricles) measured at time of diagnosis. In clinical practice, the baseline volume will normally be the volume measured at time of scan (if advisable, treatment will then be initiated as soon as possible thereafter.)

Thus, the invention in one aspect relates to the selection of such subpopulation patients.

Patients who may benefit by use of the methods of the present invention include, without limitation, patients who have suffered from spontaneous or traumatic ICH. Spontaneous ICH includes patients suffering an intracerebral bleed usually associated with the occurrence of advanced age, hypertension, or deposition of amyloid in the cerebral vasculature. ICH usually results from the rupture of a single vessel causing extensive damage to the surrounding brain tissue adjacent to the damaged vessel. Traumatic ICH may be associated with accidents resulting from e.g. motor vehicle accidents or fall from a height. The resulting contusion to the head may lead to the rupture of one or more intracerebral or extracerebral (but intracranial) vessels. Many intracranial (or extracerebral) bleedings are evacuated surgically already in the acute phase, whereas the intracerebral lesions more often are inaccessible to direct evacuation as the evacuation itself would cause significant damage to the brain tissue.

Bleeding refers to extravasation of blood from any component of the circulatory system and encompasses any bleeding (including, without limitation, excessive, uncontrolled bleeding, i.e., haemorrhaging) in connection with ICH. In one series of embodiments, the excessive bleeding is caused by spontaneous ICH; in another it is caused by traumatic ICH.

The methods of the present invention can be applied advantageously to any subpopulation patient who has suffered spontaneous or traumatic ICH that, if left untreated, would result in a significant growth of the haemorrhage and in associated oedema and/or complications.

In one series of embodiments, patients treated according to the invention do not suffer from a bleeding disorder, whether congenital or acquired, such as, e.g., Haemophilia A, B, or C.

In different embodiments of the invention, patients may be excluded from treatment if they have been diagnosed with a congenital bleeding disorder.

Factor VIIa and Factor VIIa Equivalents:

In practicing the present invention, any Factor VIIa or equivalent may be used that is effective in preventing complications when administered to a selected ICH subpopulation patient. In some embodiments, the Factor VIIa is human Factor VIIa, as disclosed, e.g., in U.S. Pat. No. 4,784,950 (wild-type Factor VII). The term "Factor VII" is intended to encompass Factor VII polypeptides in their uncleaved (zymogen) form, as well as those that have been proteolytically processed to yield their respective bioactive forms, which may be designated Factor VIIa. Typically, Factor VII is cleaved between residues 152 and 153 to yield Factor VIIa.

Factor VIIa equivalents include, without limitation, Factor VII polypeptides that have either been chemically modified relative to human Factor VIIa and/or contain one or more amino acid sequence alterations relative to human Factor VIIa. Such equivalents may exhibit different properties relative to human Factor VIIa, including stability, phospholipid binding, altered specific activity, and the like. Non-limiting examples of Factor VIIa equivalents include PEGylated human Factor VIIa, cysteine-PEGylated human Factor VIIa, and sequence variants thereof. PEGylated Factor VIIa includes, without limitation, GlycoPegylated FVII derivatives as disclosed in WO 03/31464 and US Patent applications US 20040043446, US 20040063911, US 20040142856, US 20040137557, US 20040132640, WO2007022512, and US 20070105755 (Neose Technologies, Inc.); FVII conjugates as disclosed in WO 01/04287, US patent application 20030165996, WO 01/58935, WO 03/93465 (Maxygen ApS) and WO 02/02764, US patent application 20030211094 (University of Minnesota).

In one series of embodiments, a Factor VIIa equivalent includes polypeptides that exhibit at least about 10%, preferably at least about 30%, more preferably at least about 50%, and most preferably at least about 70%, of the specific biological activity of human Factor VIIa. For purposes of the invention, Factor VIIa biological activity may be quantified by measuring the ability of a preparation to promote blood clotting using Factor VII-deficient plasma and thromboplastin, as described, e.g., in U.S. Pat. No. 5,997,864. In this assay, biological activity is expressed as the reduction in clotting time relative to a control sample and is converted to "Factor VII units" by comparison with a pooled human serum standard containing 1 unit/ml Factor VII activity. Alternatively, Factor VIIa biological activity may be quantified by (i) measuring the ability of Factor VIIa or a Factor VIIa equivalent to produce of Factor Xa in a system comprising TF embedded in a lipid membrane and Factor X. (Persson et al., J. Biol. Chem. 272:19919-19924, 1997); (ii) measuring Factor X hydrolysis in an aqueous system (see, Example 5 below); (iii) measuring the physical binding of Factor VIIa or a Factor VIIa equivalent to TF using an instrument based on surface plasmon resonance (Persson, FEBS Letts. 413:359-363, 1997) and (iv) measuring hydrolysis of a synthetic substrate by Factor VIIa and/or a Factor VIIa equivalent.

Examples of factor VII equivalents include, without limitation, wild-type Factor VII, L305V-FVII, L305V/M306D/D309S-FVII, L305I-FVII, L305T-FVII, F374P-FVII, V158T/M298Q-FVII, V158D/E296V/M298Q-FVII, K337A-FVII, M298Q-FVII, V158D/M298Q-FVII, L305V/K337A-FVII, V158D/E296V/M298Q/L305V-FVII, V158D/E296V/M298Q/K337A-FVII, V158D/E296V/M298Q/L305V/K337A-FVII, K157A-FVII, E296V-FVII, E296V/M298Q-FVII, V158D/E296V-FVII, V158D/M298K-FVII, and S336G-FVII, L305V/K337A-FVII, L305V/V158D-FVII, L305V/E296V-FVII, L305V/M298Q-FVII, L305V/V158T-FVII, L305V/K337A/V158T-FVII, L305V/K337A/M298Q-FVII, L305V/K337A/E296V-FVII, L305V/K337A/V158D-FVII, L305V/V158D/M298Q-FVII, L305V/V158D/E296V-FVII, L305V/V158T/M298Q-FVII, L305V/V158T/E296V-FVII, L305V/E296V/M298Q-FVII, L305V/V158D/E296V/M298Q-FVII, L305V/V158T/E296V/M298Q-FVII, L305V/V158T/K337A/M298Q-FVII, L305V/V158T/E296V/K337A-FVII, L305V/V158D/K337A/M298Q-FVII, L305V/V158D/E296V/K337A-FVII, L305V/V158D/E296V/M298Q/K337A-FVII, L305V/V158T/E296V/M298Q/K337A-FVII, S314E/K316H-FVII, S314E/K316Q-FVII, S314E/L305V-FVII, S314E/K337A-FVII, S314E/V158D-FVII, S314E/E296V-FVII, S314E/M298Q-FVII, S314E/V158T-FVII, K316H/L305V-FVII, K316H/K337A-FVII, K316H/V158D-FVII, K316H/E296V-FVII, K316H/M298Q-FVII, K316H/V158T-FVII, K316Q/L305V-FVII, K316Q/K337A-FVII, K316Q/V158D-FVII, K316Q/E296V-FVII, K316Q/M298Q-FVII, K316Q/V158T-FVII, S314E/L305V/K337A-FVII, S314E/L305V/V158D-FVII, S314E/L305V/E296V-FVII, S314E/L305V/M298Q-FVII, S314E/L305V/V158T-FVII, S314E/L305V/K337A/V158T-FVII, S314E/L305V/K337A/M298Q-FVII, S314E/L305V/K337A/E296V-FVII, S314E/L305V/K337A/V158D-FVII, S314E/L305V/V158D/M298Q-FVII, S314E/L305V/V158D/E296V-FVII, S314E/L305V/V158T/M298Q-FVII, S314E/L305V/V158T/E296V-FVII, S314E/L305V/E296V/M298Q-FVII, S314E/L305V/V158D/E296V/M298Q-FVII, S314E/L305V/V158T/E296V/M298Q-FVII, S314E/L305V/V158T/K337A/M298Q-FVII, S314E/L305V/V158T/E296V/K337A-FVII, S314E/L305V/V158D/K337A/M298Q-FVII, S314E/L305V/V158D/E296V/K337A-FVII, S314E/L305V/V158D/E296V/M298Q/K337A-FVII, S314E/L305V/V158T/E296V/M298Q/K337A-FVII, K316H/L305V/K337A-FVII, K316H/L305V/V158D-FVII, K316H/L305V/E296V-FVII, K316H/L305V/M298Q-FVII, K316H/L305V/V158T-FVII, K316H/L305V/K337A/V158T-FVII, K316H/L305V/K337A/M298Q-FVII, K316H/L305V/K337A/E296V-FVII, K316H/L305V/K337A/V158D-FVII, K316H/L305V/V158D/M298Q-FVII, K316H/L305V/V158D/E296V-FVII, K316H/L305V/V158T/M298Q-FVII, K316H/L305V/V158T/E296V-FVII, K316H/L305V/E296V/M298Q-FVII, K316H/L305V/V158D/E296V/M298Q-FVII, K316H/L305V/V158T/E296V/M298Q-FVII, K316H/L305V/V158T/K337A/M298Q-FVII, K316H/L305V/V158T/E296V/K337A-FVII, K316H/L305V/V158D/K337A/M298Q-FVII, K316H/L305V/V158D/E296V/K337A-FVII, K316H/L305V/V158D/E296V/M298Q/K337A-FVII, K316H/L305V/V158T/E296V/M298Q/K337A-FVII, K316Q/L305V/K337A-FVII, K316Q/L305V/V158D-FVII, K316Q/L305V/E296V-FVII, K316Q/L305V/M298Q-FVII, K316Q/L305V/V158T-FVII, K316Q/L305V/K337A/V158T-FVII, K316Q/L305V/K337A/E296V-FVII, K316Q/L305V/K337A/V158D-FVII, K316Q/L305V/V158D/M298Q-FVII, K316Q/L305V/V158D/E296V-FVII, K316Q/L305V/V158T/M298Q-FVII, K316Q/L305V/V158T/E296V-FVII, K316Q/L305V/E296V/M298Q-FVII, K316Q/L305V/V158D/E296V/M298Q-FVII, K316Q/L305V/V158T/E296V/M298Q-FVII, K316Q/L305V/V158T/K337A/M298Q-FVII, K316Q/L305V/V158T/E296V/K337A-FVII, K316Q/L305V/V158D/K337A/M298Q-FVII, K316Q/L305V/V158D/

E296V/K337A-FVII, K316Q/L305V/V158D/E296V/M298Q/K337A-FVII, and K316Q/L305V/V158T/E296V/M298Q/K337A-FVII.

Preparations and Formulations:

The present invention encompasses therapeutic administration of Factor VIIa or Factor VIIa equivalents, which is achieved using formulations that comprise Factor VIIa preparations. As used herein, a "Factor VII preparation" refers to a plurality of Factor VIIa polypeptides or Factor VIIa equivalent polypeptides, including variants and chemically modified forms, that have been separated from the cell in which they were synthesized, whether a cell of origin or a recombinant cell that has been programmed to synthesize Factor VIIa or a Factor VIIa equivalent.

Separation of polypeptides from their cell of origin may be achieved by any method known in the art, including, without limitation, removal of cell culture medium containing the desired product from an adherent cell culture; centrifugation or filtration to remove non-adherent cells; and the like.

Optionally, Factor VII polypeptides may be further purified. Purification may be achieved using any method known in the art, including, without limitation, affinity chromatography, such as, e.g., on an anti-Factor VII antibody column (see, e.g., Wakabayashi et al., *J. Biol. Chem.* 261:11097, 1986; and Thim et al., *Biochem.* 27:7785, 1988); hydrophobic interaction chromatography; ion-exchange chromatography; size exclusion chromatography; electrophoretic procedures (e.g., preparative isoelectric focusing (IEF), differential solubility (e.g., ammonium sulfate precipitation), or extraction and the like. See, generally, Scopes, *Protein Purification*, Springer-Verlag, New York, 1982; and *Protein Purification*, J.-C. Janson and Lars Ryden, editors, VCH Publishers, New York, 1989. Following purification, the preparation preferably contains less than about 10% by weight, more preferably less than about 5% and most preferably less than about 1%, of non-Factor VII proteins derived from the host cell.

Factor VII and Factor VII-related polypeptides may be activated by proteolytic cleavage, using Factor XIIa or other proteases having trypsin-like specificity, such as, e.g., Factor IXa, kallikrein, Factor Xa, and thrombin. See, e.g., Osterud et al., *Biochem.* 11:2853 (1972); Thomas, U.S. Pat. No. 4,456,591; and Hedner et al., *J. Clin. Invest.* 71:1836 (1983). Alternatively, Factor VII may be activated by passing it through an ion-exchange chromatography column, such as Mono Q® (Pharmacia) or the like. The resulting activated Factor VII may then be formulated and administered as described below.

Pharmaceutical compositions or formulations for use in the present invention comprise a Factor VIIa preparation in combination with, preferably dissolved in, a pharmaceutically acceptable carrier, preferably an aqueous carrier or diluent. A variety of aqueous carriers may be used, such as water, buffered water, 0.4% saline, 0.3% glycine and the like. The preparations of the invention can also be formulated into liposome preparations for delivery or targeting to the sites of injury. Liposome preparations are generally described in, e.g., U.S. Pat. Nos. 4,837,028, 4,501,728, and 4,975,282. The compositions may be sterilised by conventional, well-known sterilisation techniques. The resulting aqueous solutions may be packaged for use or filtered under aseptic conditions and lyophilised, the lyophilised preparation being combined with a sterile aqueous solution prior to administration.

The compositions may contain pharmaceutically acceptable auxiliary substances or adjuvants, including, without limitation, pH adjusting and buffering agents and/or tonicity adjusting agents, such as, for example, sodium acetate, sodium lactate, sodium chloride, potassium chloride, calcium chloride, etc.

Treatment Regimen:

In practicing the present invention, Factor VIIa or the Factor VIIa equivalent may be administered to a selected ICH subpopulation patient as a single dose comprising a single-dose-effective amount for preventing haemorrhage growth, and/or oedema formation and/or for treating complications, or in a staged series of doses which together comprise an effective amount for preventing or treating complications. An effective amount of Factor VIIa or the Factor VIIa equivalent (see below) refers to the amount of Factor VIIa or equivalent which, when administered in a single dose or in the aggregate of multiple doses, or as part of any other type of defined treatment regimen, produces a measurable statistical improvement in outcome, as evidenced by at least one clinical parameter associated with ICH and/or its complications (see below). When Factor VIIa equivalents are administered, an effective amount may be determined by comparing the coagulant activity of the Factor VIIa equivalent with that of Factor VIIa and adjusting the amount to be administered proportionately to the predetermined effective dose of Factor VIIa.

Administration of Factor VIIa or a Factor VIIa equivalent according to the present invention is initiated within about 3 hours, preferably within about 2.5 hours after occurrence of the ICH, such as, e.g., preferably within about 2 hours, or within about 1 hour.

Administration of a single dose refers to administration of an entire dose of Factor VIIa or the Factor VIIa equivalent as a slow bolus over a period of less than about 5 minutes. In some embodiments, the administration occurs over a period of less than about 2.5 minutes, and, in some, over less than about 1 min. Typically, a single-dose effective amount comprises at least about 15 µg/kg human Factor VIIa or a corresponding amount of a Factor VIIa equivalent, such as at least about 20 µg/kg, 40 µg/kg, 50 µg/kg, 75 µg/kg, 80 µg/kg, 90 µg/kg, or at least 160 µg/kg Factor VIIa.

It will be understood that the effective amount of Factor VIIa or Factor VIIa equivalent, as well as the overall dosage regimen, may vary according to the patient's haemostatic status, which, in turn, may be reflected in one or more clinical parameters, including, e.g., relative levels of circulating coagulation factors; amount of blood lost; rate of bleeding; haematocrit, and the like. It will be further understood that the effective amount may be determined by those of ordinary skill in the art by routine experimentation, by constructing a matrix of values and testing different points in the matrix.

For example, in one series of embodiments, the invention encompasses (i) administering a first dose of Factor VIIa or a Factor VIIa equivalent; (ii) assessing the patient's coagulation status after a predetermined time; and (iii) based on the assessment, administering a further dose of Factor VIIa or Factor VIIa equivalent if necessary. Steps (ii) and (iii) may be repeated until satisfactory haemostasis is achieved.

According to the invention, Factor VIIa or a Factor VIIa equivalent may be administered by any effective route, including, without limitation, intravenous, intramuscular, subcutaneous, mucosal, and pulmonary routes of administration. Preferably, administration is by an intravenous route.

Combination Treatments:

The present invention encompasses combined administration of an additional agent in concert with Factor VIIa or a Factor VIIa equivalent. In some embodiments, the additional agent comprises a coagulant, including, without limitation, a coagulation factor such as, e.g., Factor VIII, Factor IX, Factor V, Factor XI, or Factor XIII; or an inhibitor of the fibrinolytic system, such as, e.g., PAI-1, aprotinin, ε-aminocaproic acid or tranexamic acid. In one embodiment, the additional coagulation agent may be a Factor VIIa equivalent exhibiting different properties relative to human Factor VIIa, e.g. a variant or derivative of Factor VIIa exhibiting altered specific activity and/or in-vivo half-life, (e.g. as a "maintenance" dose to ensure haemostasis).

It will be understood that, in embodiments comprising administration of combinations of Factor VIIa with other agents, the dosage of Factor VIIa or Factor VIIa equivalent may on its own comprise an effective amount and additional agent(s) may further augment the therapeutic benefit to the patient. Alternatively, the combination of Factor VIIa or equivalent and the second agent may together comprise an effective amount for preventing complications associated with ICH. It will also be understood that effective amounts may be defined in the context of particular treatment regimens, including, e.g., timing and number of administrations, modes of administrations, formulations, etc.

Treatment Outcomes:

The present invention provides methods and compositions for preventing or attenuating haemorrhage growth, and/or oedema generation following ICH, as well as preventing and/or attenuating one or more complications of ICH. Complications include, without limitation, Cerebral Oedema, decreased quality of life including death caused by one or more of these syndromes.

In practicing the present invention, the severity of ICH and its complications may be assessed using conventional methods, such as, e.g., Imaging by CT or MR scans or the Clinical assessment scores (Scores) described herein. Assessments may be performed at least about 15 days from the start of treatment according to the invention, such as, e.g., at least about 30 days, at least about 40 days, or at least about 90 days from the start of treatment.

Organ damage or organ failure encompasses, without limitation, damage to the structure and/or damage to the functioning of the organ i.e. the brain, defined but not limited to cerebrum, cerebellar, pons, medulla, brain stem, ventricles, spinal cord or surrounding tissues. Examples of organ damage include, but are not limited to, morphological/structural damage and/or damage to the functioning of the organ such as, for example accumulation of excess fluid or proteins.

The terms "organ injury", "organ damage" and "organ failure" may be used interchangeably. Normally, organ damage results in organ failure. By organ failure is meant a decrease in organ function compared to the mean, normal functioning of a corresponding organ in a normal, healthy person. The organ failure may be a minor decrease in function (e.g., 80-90% of normal) or it may be a major decrease in function (e.g., 10-20% of normal); the decrease may also be a complete failure of organ function. Organ failure includes, without limitation, decreased biological functioning, e.g., due to tissue necrosis, fibrin deposition, haemorrhage, oedema, or inflammation and/or the complications that occur in response to these failures like brain herniation. Organ damage includes, without limitation, tissue necrosis, fibrin deposition, haemorrhage, oedema, or inflammation.

Methods for testing organ function and efficiency, and suitable biochemical or clinical parameters for such testing, are well known to the skilled clinician.

Such markers or biochemical parameters of organ function are, for example:

Brain perfusion: Measurements of Cerebral blood flow
Brain metabolism: Measurements of cerebral oxygen extraction or direct measurements of cerebral metabolic rate of oxygen (e.g., by MRS, PET or SPECT scans). Measurement of other substrates than oxygen such as glucose are also included.
Brain integrity: MRI (any and all standarized protocol sequences), CT, CTA, MRA
Brain cell electrical function as measured by EEG
Brain function by well established neuro diagnostic studies (e.g., Microdialysis, Transcranial Doppler)

Methods for testing for coagulopathy and inflammation are also well known to the skilled clinician. Such markers of a coagulopathic state are, for example, PTT, Fibrinogen depletion, elevation in TAT complexes, ATIII activity, IL-6, IL-8, or TNFR-1.

In the present context, prevention includes, without limitation, the attenuation, elimination, minimization, alleviation or amelioration of one or more symptoms or conditions associated with ICH and/or its complications, including, but not limited to, the prevention of further damage to and/or failure of the effected organ already subject to some degree of organ failure and/or damage, as well as the prevention of damage and/or failure of further organs not yet subject to organ failure and/or damage. Examples of such symptoms or conditions include, but are not limited to, morphological/structural damage and/or damage to the functioning of organs such as, but not limited to, brain and surrounding organs. Examples of such symptoms or conditions include, but are not limited to, morphological/structural damage and/or damage to the functioning of the organ(s) such as, for example, accumulation of proteins or fluids due to mass effect of the haematoma or from resulting inflammatory reactions in the surrounding tissue, tissue necrosis, fibrin deposition, haemorrhage, oedema, or inflammation.

Attenuation of organ failure or damage encompasses any improvement in organ function as measured by at least one of the well known markers of function of said organ (see below) compared to the corresponding value(s) found in selected ICH subpopulation patients not being treated in accordance with the present invention.

In various embodiments, haematoma growth is reduced by at least 5%, such as, e.g., 10%, 20%, 30%, 40%, 50%, 60%, or at least 70% compared to haematoma growth in patients not treated with Factor VIIa or a Factor VIIa equivalent in accordance with the present invention. In various embodiments, oedema generation is reduced by at least 5%, such as, e.g., 10%, 20%, 30%, 40%, 50%, 60%, or at least 70% compared to oedema generation in patients not treated with Factor VIIa or a Factor VIIa equivalent in accordance with the present invention. In other embodiments, total haemorrhage volume (ICH+IVH) is reduced by at least 5%, such as, e.g., 10%, 20%, 30%, 40%, 50%, 60%, or at least 70% compared to total haemorrhage volume in patients not treated with Factor VIIa or a Factor VIIa equivalent in accordance with the present invention.

Measurement of ICH Severity and/or Complications:

The following are non-limiting examples of instruments and methods that may be used for assessing the incidence and severity of complications of ICH in a patient:

The Glasgow Coma Score (GCS; Teasdale and Jennett, The Lancet 13; 2(7872):81-84, 1974).

The modified Rankin Scale (mRS; Bonita and Beaglehole, Stroke 1988 December; 19(12): 1497-1500).

The Barthel Index (BI; Mahoney and Barthel, Maryland State Medical Journal 1965; 14:56-61).

The NIH Stroke Scale (NIHSS; Brott et al., 1989).

The Glasgow Outcome Scale extended version (GOSe, Lindsay et al., Journal of Neurotrauma; 15 (8): 573-580, 1998).

Information of scales and assessment tools, including the five above-mentioned well-known instruments, is found at The Internet Stroke Center Washington, University School of Medicine, Department of Neurology (www.strokecenter.org).

Other Indices of Treatment:

The efficacy of the methods of the present invention may also be assessed using other clinical parameters, including, without limitation, reduction in any one or more of the following parameters relative to a similar patient who has not been administered Factor VIIa or a Factor VIIa equivalent according to the invention: an improvement in neurological outcome as determined by the NIHSS, the mRS, the E-GOS, the GCS or the BI scales as described above; a decrease in the number of days of hospitalization after suffering an ICH, including a decrease in the number of days that a patient may spend in an intensive care unit (ICU) and a decrease in the number of days in which certain interventions (such as, e.g., a ventilator) are required. Non-limiting examples of outcomes include: (i) an improvement in scores on the NIHSS by at least 1, 2, 4, 8, 10, or 20 points on the scale (ii) an improvement on the mRS scale by at least 1, 2, 3, or 4 points on the scale; (iii) an improvement on the BI scale by at least 5, 10, 15, 20 or 30 points on the scale; (iv) an improvement on the 8 point GOS by at least 1, 2, 3, 5, or 7 points on the scale (v) a decrease in ICU days by 1 day, 2 days, or 4 days; (vi) a reduction on the number of days on a ventilator by 1 day, 2 days, or 4 days; (vii) a reduction in the total days of hospitalization by 2 days, 4 days, or 8 days.

Various Embodiments of the Invention

The present invention encompasses the use of Factor VIIa or a Factor VIIa equivalent for the manufacture of a medicament for preventing or attenuating haemorrhage growth, and/or oedema generation following ICH as well as preventing or attenuating one or more complications of ICH in selected ICH subpopulation patients. Non-limiting examples of complications include: cerebral oedema and poor neurological outcome after ICH, and death. In some embodiments, the patient is suffering from spontaneous ICH and in some from traumatic ICH.

In some embodiments, the medicament comprises at least about 20 µg/kg of Factor VIIa or a corresponding amount of a Factor VIIa equivalent. In some embodiments, the medicament is for administration in a first dose containing at least about 20 µg/kg. In some embodiments, the medicament comprises at least about 80 µg/kg of Factor VIIa or a corresponding amount of a Factor VIIa equivalent. In some embodiments, the medicament is for administration in a first dose containing at least about 80 µg/kg.

In another aspect, the invention encompasses the use of Factor VIIa or a Factor VIIa equivalent for the manufacture of a medicament for reducing the number of days a selected ICH subpopulation patient is hospitalized following symptom onset or injury onset. In some embodiments, the medicament is for reducing the number of days an ICH patient spends in an Intensive Care Unit (ICU) following injury or symptom onset.

In another aspect, the invention encompasses the use of Factor VIIa or a Factor VIIa equivalent for the manufacture of a medicament for improving brain function in a selected ICH subpopulation patient. In some embodiments, the medicament is for reducing the amount of brain oedema and the associated risks of further neurological deterioration associated with such oedema in a selected ICH subpopulation patient. In some embodiments, the medicament is for reducing the risk of progression from brain injury.

In another aspect, the invention encompasses the use of Factor VIIa or a Factor VIIa equivalent for the manufacture of a medicament for reducing the risk of death in a selected ICH subpopulation patient.

In some embodiments, the medicament further comprises a second coagulation agent in an amount that augments said preventing or attenuating by the Factor VIIa or Factor VIIa equivalent. In some embodiments, the second coagulation agent is selected from the group consisting of a coagulation factor and an antifibrinolytic agent. Non-limiting examples of a coagulation factor include Factor VIII, Factor IX, Factor V, Factor XI, Factor XIII, and any combination of the foregoing; and non-limiting examples of the antifibrinolytic agent include PAI-1, aprotinin, $\epsilon$-aminocaproic acid, and tranexamic acid.

In another aspect, the invention provides kits of parts for preventing or attenuating haemorrhage growth, and/or oedema generation following ICH as well as preventing or attenuating one or more complications of ICH, comprising (i) A medicament comprising Factor VIIa or a Factor VIIa equivalent; and (ii) Instructions for Use describing that:

a. The patient experiencing ICH should be assessed as suitable for treatment with Factor VIIa or a Factor VIIa equivalent, i.e. selected as a ICH patient exhibiting one or more of the following characteristics: age$\leq$70, baseline ICH volume$\leq$60 mL, baseline IVH volume$\leq$5 mL, and elapsed time since onset of symptoms of less than about 2.5 hours;

b. A first dose containing at least about 20, preferably at least about 80 ug/kg or 160 ug/kg Factor VIIa or a corresponding amount of a Factor VIIa equivalent, should be administered at the start of treatment;

c. A second dose may be needed and may be in the amounts of 20, 40, 80 or 160 µg/kg Factor VIIa or a corresponding amount of a Factor VIIa equivalent should be administered one hour after the start of treatment.

In another aspect, the invention provides methods for preventing or attenuating haemorrhage growth, and/or oedema generation following ICH as well as preventing or attenuating one or more complications of ICH in a selected ICH subpopulation patient, the methods comprising administering to a patient in need of said preventing or attenuating an effective amount for the preventing or attenuating of Factor VIIa or a Factor VIIa equivalent. Non-limiting examples of complications include: brain death, brain herniation, respiratory compromise secondary to brain herniation and any other related complications secondary to brain dysfunction. In some embodiments, the patient is suffering from spontaneous ICH and in others from traumatic ICH.

In some embodiments, the effective amount comprises at least about 20 µg/kg of Factor VIIa or a corresponding amount of a Factor VIIa equivalent. In some embodiments, a first amount of at least about 80 µg/kg Factor VIIa or a corresponding amount of a Factor VIIa equivalent is administered at the start of treatment, and a second amount of about 20, 40, 80 or 160 µg/kg of Factor VIIa or a corresponding amount of a Factor VIIa equivalent is administered to the patient one hour after the start of treatment. In some embodiments, the method further comprises administering to the patient a second coagulation agent in an amount that augments the preventing or attenuating by Factor VIIa or a Factor VIIa equivalent. In some embodiments, the second coagulation agent is a coagulation factor or an antifibrinolytic agent. Non-limiting examples of a coagulation factor include Factor VIII, Factor IX, Factor XIII, and any combination of the foregoing; and non-limiting examples of an antifibrinolytic agent include PAI-1, aprotinin, ε-aminocaproic acid, and tranexamic acid.

In another aspect, the invention provides methods for reducing the number of days a selected ICH subpopulation patient is hospitalized following spontaneous ICH or traumatic ICH, which are carried out by administering to the patient an effective amount for the reduction of Factor VIIa or a Factor VIIa equivalent.

In another aspect, the invention provides methods for reducing the number of days a selected ICH subpopulation patient spends in an Intensive Care Unit (ICU) following injury or symptom onset, which are carried out by administering to the patient an effective amount for the reduction of Factor VIIa or a Factor VIIa equivalent.

In another aspect, the invention provides methods for improving brain function in a selected ICH subpopulation patient, which is carried out by administering to the patient an effective amount for the improving of Factor VIIa or a Factor VIIa equivalent.

In another aspect, the invention provides methods for reducing the risk of developing complications of brain dysfunction including, but not limited to brain herniation, brain infarction in a selected ICH subpopulation patient, which methods are carried out by administering to the patient an effective amount for the reducing of Factor VIIa or a Factor VIIa equivalent. In some embodiments, the invention provides methods for reducing the risk of progression from brain injury to brain death.

In another aspect, the invention provides methods for reducing the risk of death in a selected ICH subpopulation patient, which is carried out by administering to the patient an effective amount for the reducing of Factor VIIa or a Factor VIIa equivalent.

In another aspect, the invention provides methods for preventing or attenuating haemorrhage growth, and/or oedema generation following ICH in a selected ICH subpopulation patient, which are carried out by intentionally administering to a patient in need of the preventing or attenuating an effective amount for the preventing or attenuating of Factor VIIa or a Factor VIIa equivalent for the purpose of preventing or attenuating the haemorrhage growth, and/or oedema generation.

In another aspect, the invention provides methods for preventing or attenuating haemorrhage growth, and/or oedema generation following ICH in a majority of spontaneous ICH or traumatic selected ICH subpopulation patients, which are carried out by (i) administering to a group of selected ICH subpopulation patients an effective amount for the preventing or attenuating of Factor VIIa or a Factor VIIa equivalent; and (ii) observing a reduction in the frequency of occurrence of one or more complications of ICH among the group of patients relative to the frequency of occurrence of the complications that would have been expected in the same group of patients who had not received the Factor VIIa or Factor VIIa equivalent.

Various Embodiments of the Invention are Described in the Following:

1. A method for preventing or attenuating one or more complications of intracerebral haemorrhage (ICH), the method comprising:
(i) selecting an ICH patient who exhibits one or more of the following characteristics: age≦70, baseline ICH volume≦60 mL, baseline IVH volume≦5 mL, and elapsed time since onset of symptoms of less than about 2.5 hours;
(ii) administering to said patient in need thereof an effective amount of a first coagulation agent comprising Factor VIIa or a Factor VIIa equivalent.

2. The method according to embodiment 1, wherein said ICH patient exhibits two or more of the following exhibits: age≦70, baseline ICH volume≦60 mL, baseline IVH volume≦5 mL, and elapsed time since onset of symptoms of less than about 2.5 hours.

3. The method according to embodiment 2, wherein said ICH patient exhibits three or more of the following exhibits: age≦70, baseline ICH volume≦60 mL, baseline IVH volume≦5 mL, and elapsed time since onset of symptoms of less than about 2.5 hours.

4. The method according to embodiment 3, wherein said ICH patient exhibits all of the following exhibits: age≦70, baseline ICH volume≦60 mL, baseline IVH volume≦5 mL, and elapsed time since onset of symptoms of less than about 2.5 hours.

5. The method according to embodiment 1, wherein said patient has experienced spontaneous or traumatic ICH.

6. The method according to embodiment 1, wherein said effective amount comprises at least about 20 μg/kg of said Factor VIIa or Factor VIIa equivalent.

7. The method according to embodiment 6, wherein the effective amount comprises at least about 80 μg/kg Factor VIIa or Factor VIIa equivalent.

8. The method according to embodiment 1, further comprising administering to the patient a second coagulation agent, wherein the amounts of said first and second coagulation agents together are effective in said preventing or attenuating.

9. The method according to embodiment 8, wherein said second coagulation agent is a coagulation factor.

10. The method according to embodiment 8, wherein said second coagulation agent is an antifibrinolytic agent.

11. The method according to embodiment 1, wherein said administering results in one or more of: reduction in the number of days an ICH patient is hospitalized following ICH and a reduction in the risk of death in an ICH patient.

12. A method for assessing the suitability of an ICH patient for treatment with Factor VIIa or a Factor VIIa equivalent, the method comprising selecting an ICH patient who exhibits one or more of the following characteristics: Age≦70, baseline ICH volume≦60 mL, baseline IVH volume≦5 mL, and elapsed time since onset of symptoms of less than about 2.5 hours.

13. The method of embodiment 12, wherein said patient exhibits two or more of the following characteristics: Age≦70, baseline ICH volume≦60 mL, baseline IVH volume≦5 mL, and elapsed time since onset of symptoms of less than about 2.5 hours.

14. The method of embodiment 13, wherein said patient exhibits three or more of the following characteristics: Age≦70, baseline ICH volume≦60 mL, baseline IVH volume≦5 mL, and elapsed time since onset of symptoms of less than about 2.5 hours.

15. The method of embodiment 14, wherein said patient exhibits all of the following characteristics: Age≦70, baseline ICH volume≦60 mL, baseline IVH volume≦5 mL, and elapsed time since onset of symptoms of less than about 2.5 hours.

16. The method according to embodiment 12 wherein said patient has experienced spontaneous or traumatic ICH.

17. Use of a first coagulation agent comprising Factor VIIa or a Factor VIIa equivalent for the manufacture of a medicament for preventing or attenuating one or more complications of intracerebral haemorrhage (ICH), where said medicament is administered to a selected ICH patient who exhibits one or more of the following characteristics: Age≦70, baseline ICH volume≦60 mL, baseline IVH volume≦5 mL, and elapsed time since onset of symptoms of less than about 2.5 hours.

18. The use according to embodiment 17, wherein said patient exhibits two or more of the following characteristics: Age≦70, baseline ICH volume≦60 mL, baseline IVH volume≦5 mL, and elapsed time since onset of symptoms of less than about 2.5 hours.

19. The use according to embodiment 18, wherein said patient exhibits three or more of the following characteristics: Age≦70, baseline ICH volume≦60 mL, baseline IVH volume≦5 mL, and elapsed time since onset of symptoms of less than about 2.5 hours.

20. The use according to embodiment 19, wherein said patient exhibits all of the following characteristics: Age≦70, baseline ICH volume≦60 mL, baseline IVH volume≦5 mL, and elapsed time since onset of symptoms of less than about 2.5 hours.

21. The use according to embodiment 17 wherein said patient has experienced spontaneous or traumatic ICH.

22. The use according to embodiment 17, wherein the administered amount of Factor VIIa or a Factor VIIa equivalent comprises at least about 20 μg/kg.

23. The use according to embodiment 22, wherein the administered amount of Factor VIIa or a Factor VIIa equivalent comprises at least about 80 μg/kg.

24. The use according to embodiment 17, further comprising administering to the patient a second coagulation agent, and wherein the amounts of said first and second coagulation agents together are effective in said preventing or attenuating.

25. The use according to embodiment 24, wherein said second coagulation agent is a coagulation factor.

26. The use according to embodiment 24, wherein said second coagulation agent is an antifibrinolytic agent.

27. The use according to embodiment 17, wherein said preventing or attenuating results in one or more of: reduction in the number of days an ICH patient is hospitalized following ICH and a reduction in the risk of death in an ICH patient.

28. A first coagulation agent comprising Factor VIIa or a Factor VIIa equivalent for use in preventing or attenuating one or more complications of intracerebral haemorrhage (ICH), wherein said coagulation agent is administered to a selected ICH patient who exhibits one or more of the following characteristics: Age≦70, baseline ICH volume≦60 mL, baseline IVH volume≦5 mL, and elapsed time since onset of symptoms of less than about 2.5 hours.

29. The coagulation agent according to embodiment 28, wherein said patient exhibits two or more of the following characteristics: Age≦70, baseline ICH volume≦60 mL, baseline IVH volume≦5 mL, and elapsed time since onset of symptoms of less than about 2.5 hours.

30. The coagulation agent according to embodiment 29, wherein said patient exhibits three or more of the following characteristics: Age≦70, baseline ICH volume≦60 mL, baseline IVH volume≦5 mL, and elapsed time since onset of symptoms of less than about 2.5 hours.

31. The coagulation agent according to embodiment 30, wherein said patient exhibits all of the following characteristics: Age≦70, baseline ICH volume≦60 mL, baseline IVH volume≦5 mL, and elapsed time since onset of symptoms of less than about 2.5 hours.

32. The coagulation agent according to embodiment 28, wherein said patient has experienced spontaneous or traumatic ICH.

33. The coagulation agent according to embodiment 28, wherein the administered amount of Factor VIIa or a Factor VIIa equivalent comprises at least about 20 μg/kg.

34. The coagulation agent according to embodiment 33, wherein the administered amount of Factor VIIa or a Factor VIIa equivalent comprises at least about 80 μg/kg.

35. The coagulation agent according to embodiment 28, further comprising a second coagulation agent wherein the amounts of said first and second coagulation agents together are effective in said preventing or attenuating.

36. The coagulation agent according to embodiment 35, wherein said second coagulation agent is a coagulation factor.

37. The coagulation agent according to embodiment 35, wherein said second coagulation agent is an antifibrinolytic agent.

38. The coagulation agent according to embodiment 28, wherein said preventing or attenuating results in one or more of: reduction in the number of days an ICH patient is hospitalized following ICH and a reduction in the risk of death in an ICH patient.

The following examples are intended as non-limiting illustrations of the present invention.

EXAMPLES

General Methods

Methods of Measurement.

Haematoma, Intraventricular Haemorrhage (IVH) and oedema volumes ($mm^3$) were measured by computed tomography scan (CT scan) using Analyze™ software (Biomedical Imaging Resource at the Mayo Foundation) equipped with a ROI (region of interest) module.

Haematoma, Intraventricular Haemorrhage (IVH) and oedema volumes ($mm^3$) were calculated by a neuroradiologist blinded to treatment allocation at a centralized location by tracing the perimeter of appropriate high- or low-attenuation zone in each involved cross-sectional image ("slice") using a computerized imaging system. All measurements will be made using the Region of Interest (ROI) module within the Analyze™ software. The reviewer will define each target area using the semi-automated segmentation and/or freehand tracing tools. Each defined area will be editable to aid the reviewer to include only the area of interest, which is represented as a ROI on the image. This procedure will be reproduced for each slice as well as each separate target area the reviewer determines is necessary.

Once all areas have been defined by the reviewer, Analyze™ software will be used to calculate statistics of each ROI. This is to include the area of the ROI, defined in $mm^2$ and the volume of the ROI, defined in $mm^3$. The volume of the ROI is calculated by multiplying the slice thickness of the acquisition by the area. Since an object may include more then one slice, the ROI volume for each slice is displayed in a "Stat Log Region of Interest" window. This information in this window is saved as an ASCII file and directly imported into the Blind Read Database. Once all volumes have been imported into the Blind Read Database, the reviewer-defined regions are stored as object maps and saved. An object map is simply a copy of the volume with defined areas/structures.

The reviewer will use the Region of Interest (ROI) module from the Analyze™ software to measure the following:

The volume of ICH.
The volume of Intraventricular Haemorrhage (IVH).
The total volume of Perihematoma oedema.

Based upon the above measurements the following will be calculated:

The change in ICH volume from the screening to the 24 hour CT scan expressed in $mm^3$ and percent.

Calculated as change in percent=[(ICH volume at 24 hours−ICH volume at screening)/ICH volume at screening]100.

Calculated as change in millimeters$^3$=ICH volume at 24 hours−ICH volume at screening Ratio of oedema/ICH volume at each CT scan Ratio=volume of oedema/ICH volume Total Haemorrhage at each CT scan.

Calculated as Total Haemorrhage=ICH+IVH

The following calculations will be used on CT scans submitted using multi-slice thickness techniques. (A smaller slice thickness used through the posterior fossa with a transition to a larger slice thickness through to the vertex.)
1=Smaller Slice Thickness Acquisition
2=Larger slice Thickness Acquisition Calculated as Slice Thickness (mm)/Slice Spacing (mm)=$X$/[Table Position 1 (mm)+½ Slice Spacing 1 (mm)]−[Table Position 2 (mm)−½ Slice Spacing 2 (mm)]

Volume of Gap/Overlap in millimeters$^3$=$X$ (Area of final slice in 1 in millimeters$^2$)

Another simplified method that is able to provide a reasonable estimate of ICH volumes is the ABC/2 method, in which A is the greatest diameter on the largest haemorrhage slide, B is the diameter perpendicular to A, and C is the approximate number of axial slides with haemorrhage multiplied by the slice thickness (Kotharin, R U., Brott, T., Broderick, J P., Barsan, W G, Sauerbeck, L R. Zuccarello, M and Khoury, J. The ABCs of measuring intracerebral haemorrhage volumes. Stroke, 1966; 27:1304__1305). The presence or absence of IVH can also be noted on the basis of the baseline CT scan.

WORKING EXAMPLES

Example 1

Treatment of Subpopulation of ICH Patients with Recombinant Activated Factor VII Objectives:
To confirm a Phase 2b study in which recombinant activated factor VII (rFVIIa) reduced haematoma growth and improved survival and functional outcome.
Trial Design:
The trial was a randomized, multicenter, double-blind, placebo-controlled trial with three treatment arms: doses of 20 and 80 μg/kg against placebo.
We randomly assigned 841 spontaneous ICH patients diagnosed by CT scan within 3 hours of symptom onset to receive placebo (N=268), 20 μg/kg (N=276), or 80 μg/kg (N=297) rFVIIa. Treatment was given within 4 hour of the baseline CT scan. The primary endpoint was severe disability or death (modified Rankin Scale [mRS] score of 5 or 6) at day 90.
Patients Enrolled in Study:
Patients aged$\leq$18 years with spontaneous ICH documented by CT scan within three hours of symptom onset were eligible for enrolment. Exclusion criteria included: GCS score of $\leq$5; surgical haematoma evacuation planned within 24 hours of admission; secondary ICH due to aneurysm, arteriovenous malformation, trauma, or other causes; known oral anticoagulant use or thrombocytopenia; history of coagulopathy; acute sepsis, crush injury, or disseminated intravascular coagulation; pregnancy; prior disability (pre-ICH modified Rankin Scale score>2); and known recent thrombotic or vasoocclusive disease (ie, angina, claudication, deep vein thrombosis [DVT], or cerebral or myocardial infarction [MI]).
Study Intervention:
Patients were block randomized by site, using sequentially numbered containers to receive a single intravenous dose of placebo, 20 μg/kg, or 80 μg/kg of rFVIIa (NovoSeven®, Novo Nordisk A/S, Bagsvaerd, Denmark). Treatment was administered within one hour of the baseline CT and no later than four hours after symptom onset. The study drug was supplied as a freeze-dried powder and was reconstituted in sterile water before being administered intravenously over one to two minutes. Dosing was calculated based on estimated body weight. It was recommended that all aspects of medical management conform with the 1999 American Stroke Association guidelines for ICH.
CT Image Analysis:
Follow-up CT scans were performed 24±3 and 72±6 hours after drug administration. When a 24-hour scan was not available within the specified time period, the first follow-up scan performed within 48 hours was analyzed, when available. Digital CT data were transmitted to an imaging laboratory (Bio-Imaging Technologies Inc, Newtown, Pa.) and assessed using Analyze™ software (Mayo Clinic, Rochester, Minn.) by two neuroradiologists who were blinded to treatment. ICH, intraventricular haemorrhage (IVH), and oedema volumes were calculated using computerized planimetric techniques and were evaluated as secondary endpoints. Interobserver reliability of this method is excellent, with an intraclass correlation coefficient of 0.96 for ICH and 0.95 for IVH.
Clinical Assessments:
Clinical assessments were performed at enrolment, one and 24 hours after drug administration, on days 2, 3, and 15 (or discharge if earlier) during hospitalization, and on day 90. Neurological deficit was assessed during hospitalization using the GCS and National Institutes of Health Stroke Scale (NIHSS). The primary outcome measure was the modified Rankin Scale (mRS) at day 90. The mRS evaluates global functional outcome; scores range from 0, indicating full recovery, to 6, for death. Secondary endpoints evaluated at day 90 included the Barthel Index (BI), the Extended Glasgow Outcome Scale (E-GOS), the NIHSS, the European Quality of Life scale (EuroQOL), and the Revised Hamilton Depression Scale
Statistical Analysis:
All analyses were based on intention-to-treat (ITT). The primary efficacy endpoint was severe disability or death, defined as a mRS score of 5 or 6 at day 90. We powered this study to detect an odds ratio of poor outcome of 0.53 or less with active treatment compared to placebo (assuming a frequency of 45% in placebo and 30% with treatment) based on a one-sided chi-square test, with a beta of 0.90 and alpha of 0.025. Based on a planned interim sample size review evaluating the proportion of patients in the pooled placebo and 80 μg/kg groups with day 90 mRS scores of 5 or 6, midway through the study the study population was increased by 123 patients to maintain 90% power. The primary outcome measure was analyzed using logistic regression with treatment, age, gender, baseline ICH volume, pre-stroke mRS, and location (supra-versus infratentorial) as covariates according to a pre-specified statistical analysis plan. For surviving patients with missing outcome data, the last observation was carried forward. The ranks of the BI and NIHSS were analyzed using an ANOVA model with the same covariates, except that baseline GCS was used instead of the mRS.
CT lesion volumes were analyzed using generalized linear mixed models to yield estimated mean values. Subject and reader (two neuroradiologists) were included as random effects, and treatment, baseline ICH volume, onset-to-CT interval, and CT-to-needle interval were included as fixed-effect covariates. Percent changes were log-transformed to obtain normality after adding 100 to eliminate negative values. The X2 test was used to compare the frequency of arterial, venous, and all thromboembolic SAEs in the three treatment groups at day 90. All analyses were performed using SAS® on a UNIX platform (version 8.2, SAS Institute, Cary, N.C.).

Trial Product(s):
Activated recombinant human factor VII (rFVIIa/NovoSeven®) and placebo are supplied by Novo Nordisk A/S, Denmark as freeze-dried powders to be reconstituted with water for injection.

Introduction: The recombinant activated Factor VII (rFVIIa) FAST was a randomized, double-blind placebo-controlled study of 821 spontaneous intracerebral haemorrhage (ICH) patients diagnosed by computed tomography (CT) scan≦3 hours after symptom onset and treated with placebo, 20 or 80 µg/kg rFVIIa≦1 h after CT. FAST showed that rFVIIa (80 µg/kg) given≦4 hours after ICH onset significantly limits haematoma growth.

Methods: Several combinations of predictive factors for outcome after ICH were analyzed at different clinically meaningful cut-offs to identify a candidate subgroup. The impact of treatment on outcome and volume change in this group was analyzed by logistic regression (mRS) and generalized linear mixed models (ICH volumes). The same criteria were then applied to the phase 2b trial to examine our hypothesis of the assumed responder group.

Results: A candidate responder subgroup (n=160) was identified comprising patients aged≦70 years, with baseline ICH volume<60 ml, baseline IVH volume<5 ml, and time from symptom onset to rFVIIa treatment≦2.5 h. The adjusted odds ratio (OR) for poor outcome with rFVIIa treatment in this group was 0.28 (95% CI 0.08 to 1.06). The reduction in hemorrhage growth relative to placebo was almost doubled by limiting onset to treatment to 2.5 hours (−7.3±3.2 ml [P=0.03] versus −3.8±1.5 ml in the 80 µg/kg group overall). The observed treatment effect was then confirmed in an analysis of the same patient subgroup (n=56) in the earlier phase 2b study.

Conclusions: This exploratory analysis provides evidence for the prognostic impact of age, baseline ICH and IVH, and timing to treatment on 90 day outcomes, and suggests that a subpopulation of ICH patients may benefit from haemostatic treatment with rFVIIa.

Example 2

Factor VIIa Administration to ICH Subpopulation Patients

Post-Hoc Analyses, Trial F7ICH-1641
A sub-population of patients was identified post hoc, excluding patients in whom trial drug intervention would be unlikely to be successful due to poor prognosis at baseline. Selection criteria for the identified sub-population comprised age≦70 years, baseline ICH volume<60 mL, baseline IVH volume<5 mL and time from symptom onset to trial drug administration≦2.5 hours. The estimated odds ratio for suffering a poor outcome was reduced to 0.28 in the 80 µg/kg rFVIIa group relative to placebo (p=0.0309; one-sided test), see Table 5-5.

TABLE 5-5

Analysis of Proportion of Subject with Poor Outcome*
at Day 90, Trial F7ICH-1641 Sub-population

|  | N | (%) | OR | 95% CI | p-value |
| --- | --- | --- | --- | --- | --- |
| Placebo | 11 | 19% n | 1.00 | [.; .] | . |
| 20 ug/kg | 6 | 13% | 0.36 | [0.10; 1.33] | 0.0632 |
| 80 ug/kg | 5 | 9% | 0.28 | [0.08; 1.06] | 0.0309 |

*modified Rankin Scale score 5 + 6 (severe disability or death)
N = Number with poor outcome, OR = Odds Ratio, p-value is from the one-sided test
The model includes treatment group, age, gender, mRS at baseline, and ICH volume at baseline as covariates. Location was not adjusted for as this gave rise to a questionable model fit The improved clinical outcome in the sub-population of patients was reflected in results across investigated clinical endpoints and corresponded with a more pronounced haemostatic effect, see Table 5-6. The haematoma expands the most during the early hours following onset and the more pronounced haemostatic effect seen in these patients was likely a consequence of having received trial drug within 2.5 hours of symptom onset. It follows that the earlier the patient receives rFVIIa, the greater is the opportunity of rFVIIa to limit haematoma expansion.

TABLE 5-6

Analysis of Percent Change in ICH Volume (%) from Baseline
to 24 Hours after Dosing, Trial F7ICH-1641 Sub-population
Estimated 95% CI Estimated Rate-Ratio 95% CI p-value
mean percent Ratio* for comparison with placebo**

| Placebo | 39.21 | [24.29; 55.93] | 1.39 | 1.00 | [.; .] | . |
| --- | --- | --- | --- | --- | --- | --- |
| 20 ug/kg | 24.49 | [9.75; 41.20] | 1.24 | 0.89 | [0.75; 1.06] | 0.1953 |
| 80 ug/kg | 13.88 | [1.56; 27.69] | 1.14 | 0.82 | [0.70; 0.96] | 0.0149 |

*The ratio is the post baseline volume for the evaluated time point divided by the baseline volume
**The treatment difference is expressed as the ratio between the treatment group ratio and the placebo ratio
The model includes ICH volume at baseline, time from stroke to baseline CT scan, time from baseline CT scan to dosing and treatment group as fixed effects. Subject and reader are included as random effects All patents, patent applications, and literature references referred to herein are hereby incorporated by reference in their entirety.

Many variations of the present invention will suggest themselves to those skilled in the art in light of the above detailed description. Such obvious variations are within the full intended scope of the appended claims.

The invention claimed is:

1. A method for preventing or attenuating one or more complications of intracerebral haemorrhage (ICH) in an ICH patient, the method comprising:
   (i) selecting an ICH patient who has the following characteristics: (i) Age≦70, (ii) baseline ICH volume≦60 mL, (iii) baseline intraventricular haemorrhage (IVH) volume≦5 mL, and (iv) elapsed time since onset of symptoms of less than about 2.5 hours;
   (ii) administering to said patient in need thereof an effective amount of a first coagulation agent comprising Factor VIIa or a Factor VIIa equivalent; and
   (iii) reducing growth of a haematatoma in said patient.

2. The method according to claim 1, wherein said patient has experienced spontaneous or traumatic ICH.

3. The method according to claim 1, wherein said effective amount comprises at least about 20 µg/kg of said Factor VIIa or Factor VIIa equivalent.

4. The method according to claim 3, wherein the effective amount comprises at least about 80 µg/kg Factor VIIa or Factor VIIa equivalent.

5. The method according to claim 1, further comprising administering to the patient a second coagulation agent, wherein the amounts of said first and second coagulation agents together are effective in said preventing or attenuating.

6. The method according to claim 5, wherein said second coagulation agent is a coagulation factor.

7. The method according to claim 5, wherein said second coagulation agent is an antifibrinolytic agent.

8. The method according to claim 1, wherein said administering results in one or more of: reduction in the number of days an ICH patient is hospitalized following ICH and a reduction in the risk of death in an ICH patient.

* * * * *

UNITED STATES PATENT AND TRADEMARK OFFICE
CERTIFICATE OF CORRECTION

| | | |
|---|---|---|
| PATENT NO. | : 8,354,377 B2 | Page 1 of 1 |
| APPLICATION NO. | : 12/812684 | |
| DATED | : January 15, 2013 | |
| INVENTOR(S) | : Skolnick et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 226 days.

Signed and Sealed this
Eleventh Day of November, 2014

Michelle K. Lee
*Deputy Director of the United States Patent and Trademark Office*